United States Patent
Zhou et al.

(10) Patent No.: US 9,387,256 B2
(45) Date of Patent: Jul. 12, 2016

(54) TISSUE TARGETING

(75) Inventors: He Zhou, Beijing (CN); Edward Cochran, Marshfield, MA (US); Takashi Kei Kishimoto, Lexington, MA (US)

(73) Assignee: MOMENTA PHARMACEUTICALS, INC., Cambridge, MA (US)

( * ) Notice: Subject to any disclaimer, the term of this patent is extended or adjusted under 35 U.S.C. 154(b) by 880 days.

(21) Appl. No.: 13/641,278

(22) PCT Filed: Apr. 15, 2011

(86) PCT No.: PCT/US2011/032771
§ 371 (c)(1),
(2), (4) Date: Feb. 26, 2013

(87) PCT Pub. No.: WO2011/130697
PCT Pub. Date: Oct. 20, 2011

(65) Prior Publication Data
US 2013/0156698 A1    Jun. 20, 2013

Related U.S. Application Data

(60) Provisional application No. 61/325,146, filed on Apr. 16, 2010.

(51) Int. Cl.
| | |
|---|---|
| A61K 9/00 | (2006.01) |
| A61K 47/48 | (2006.01) |
| A61K 31/00 | (2006.01) |
| A61K 31/727 | (2006.01) |
| A61K 49/00 | (2006.01) |
| A61K 51/06 | (2006.01) |

(52) U.S. Cl.
CPC .......... *A61K 47/4823* (2013.01); *A61K 31/00* (2013.01); *A61K 31/727* (2013.01); *A61K 49/0054* (2013.01); *A61K 51/065* (2013.01)

(58) Field of Classification Search
CPC ................................................ A61K 47/4823
See application file for complete search history.

(56) References Cited

U.S. PATENT DOCUMENTS

| | | | |
|---|---|---|---|
| 3,118,816 | A | 1/1964 | Gushing et al. |
| 4,235,871 | A | 11/1980 | Papahadjopoulos et al. |
| 4,303,651 | A | 12/1981 | Lindahl et al. |
| 4,629,699 | A | 12/1986 | Bianchini |
| 4,717,719 | A | 1/1988 | Sportoletti et al. |
| 4,727,063 | A | 2/1988 | Naggi et al. |
| 4,847,338 | A | 7/1989 | Linhardt et al. |
| 4,868,103 | A | 9/1989 | Stavrianopoulos et al. |

(Continued)

FOREIGN PATENT DOCUMENTS

| | | |
|---|---|---|
| BE | 620906 | 11/1962 |
| CN | 1060599 A | 4/1992 |

(Continued)

OTHER PUBLICATIONS

Goodman and Gilman's, "The Pharmacological Basis of Therapeutics" published by the McGraw-Hill Companies, Inc. pp. 5-8, 2001.

(Continued)

*Primary Examiner* — Paul Dickinson
(74) *Attorney, Agent, or Firm* — Lando & Anastasi, LLP

(57) ABSTRACT

Methods and compositions related to targeting agents to tumor tissue are described.

32 Claims, 6 Drawing Sheets

(56) References Cited

U.S. PATENT DOCUMENTS

| | | | |
|---|---|---|---|
| 4,916,219 A | 4/1990 | Linhardt et al. |
| 4,990,502 A | 2/1991 | Lormeau et al. |
| 5,262,403 A | 11/1993 | Nicolson et al. |
| 5,264,425 A | 11/1993 | Dal Pozzo et al. |
| 5,296,471 A | 3/1994 | Holme et al. |
| 5,403,827 A | 4/1995 | De-Ambrosi |
| 5,541,166 A | 7/1996 | Parish et al. |
| 5,583,121 A | 12/1996 | Chaudry et al. |
| 5,668,116 A | 9/1997 | Cullis-Hill et al. |
| 5,668,118 A | 9/1997 | Kennedy |
| 5,690,910 A | 11/1997 | Ahmed et al. |
| 5,696,100 A | 12/1997 | Holme et al. |
| 5,707,974 A | 1/1998 | Kennedy |
| 5,733,893 A | 3/1998 | Ornitz |
| 5,763,421 A | 6/1998 | Caretto et al. |
| 5,767,269 A | 6/1998 | Hirsh et al. |
| 5,795,875 A | 8/1998 | Holme et al. |
| 5,808,021 A | 9/1998 | Holme et al. |
| 5,912,237 A | 6/1999 | Kennedy |
| 5,990,097 A | 11/1999 | Kennedy |
| 6,001,820 A | 12/1999 | Hirsh et al. |
| 6,077,683 A | 6/2000 | Kennedy |
| 6,127,347 A | 10/2000 | Chaudry et al. |
| 6,130,210 A | 10/2000 | Caretto et al. |
| 6,150,342 A | 11/2000 | Mattsson et al. |
| 6,545,136 B1 | 4/2003 | Hara et al. |
| 6,596,705 B1 | 7/2003 | Varki et al. |
| 7,781,416 B2 | 8/2010 | Casu et al. |
| 7,790,700 B2 | 9/2010 | Casu et al. |
| 8,067,555 B2 | 11/2011 | Casu et al. |
| 8,071,569 B2 | 12/2011 | Mousa |
| 8,569,262 B2 | 10/2013 | Sundaram et al. |
| 8,592,393 B2 | 11/2013 | Sundaram et al. |
| 2003/0013682 A1 | 1/2003 | Banito et al. |
| 2003/0147848 A1 | 8/2003 | Geng |
| 2004/0056249 A1 | 3/2004 | Russell et al. |
| 2004/0087544 A1 | 5/2004 | Russo et al. |
| 2005/0107331 A1 | 5/2005 | Banito et al. |
| 2005/0137167 A1 | 6/2005 | Casu et al. |
| 2005/0222084 A1 | 10/2005 | Casu et al. |
| 2005/0282775 A1 | 12/2005 | Kennedy |
| 2006/0040896 A1 | 2/2006 | Kennedy |
| 2006/0172968 A1 | 8/2006 | Casu et al. |
| 2007/0037814 A1 | 2/2007 | Rawson et al. |
| 2007/0142323 A1 | 6/2007 | Viskov et al. |
| 2008/0051567 A1 | 2/2008 | Casu et al. |
| 2008/0280819 A1 | 11/2008 | Mulugeta et al. |
| 2009/0012165 A1 | 1/2009 | Ueno |
| 2009/0149424 A1 | 6/2009 | Byun et al. |
| 2010/0021416 A1 | 1/2010 | Lichter et al. |
| 2010/0081629 A1 | 4/2010 | Viskov et al. |
| 2010/0316640 A1 | 12/2010 | Sundaram et al. |
| 2010/0331746 A1 | 12/2010 | Deslandes |
| 2011/0076729 A1 | 3/2011 | Mamuwala et al. |
| 2011/0207919 A1 | 8/2011 | Beccati et al. |
| 2011/0288046 A1 | 11/2011 | Venkataraman et al. |

FOREIGN PATENT DOCUMENTS

| | | | |
|---|---|---|---|
| EP | 0121067 A1 | 10/1984 |
| EP | 0140781 A2 | 5/1985 |
| EP | 0346810 A2 | 12/1989 |
| EP | 0557887 A2 | 9/1993 |
| EP | 0735050 B1 | 10/1996 |
| EP | 1129718 A2 | 9/2001 |
| EP | 1268558 A1 | 1/2003 |
| JP | 60115525 | 6/1985 |
| JP | 2002-501613 A | 1/2002 |
| JP | 2006501815 A | 1/2006 |
| JP | 2007-517771 A | 7/2007 |
| JP | 2008150441 A | 7/2008 |
| JP | 2009538386 A | 11/2009 |
| JP | 2010532314 A | 10/2010 |
| WO | 9012561 A1 | 11/1990 |
| WO | 9201003 A1 | 1/1992 |
| WO | 9202232 A1 | 2/1992 |
| WO | 9217187 A1 | 10/1992 |
| WO | 9217188 A1 | 10/1992 |
| WO | 9218545 A1 | 10/1992 |
| WO | 9629973 A2 | 10/1996 |
| WO | 0155221 A1 | 8/2001 |
| WO | 02083086 A1 | 10/2002 |
| WO | 03022291 A1 | 3/2003 |
| WO | 2007001409 A2 | 1/2007 |
| WO | 2007014049 A2 | 2/2007 |
| WO | 2007056218 A2 | 5/2007 |
| WO | 2007059313 A1 | 5/2007 |
| WO | 2007144144 A1 | 12/2007 |
| WO | 2009007224 A1 | 1/2009 |
| WO | 2009059283 A1 | 5/2009 |
| WO | 2011130572 A1 | 10/2011 |

OTHER PUBLICATIONS

Johnson et al., "Can Cancer Tumors Be Starved to Death"? Retrieved Sep. 20, 2012 (online) <http://www.mhhe.com/biosci/genbio/tlw3/virtual_labs/lab6/labs/resources/original.pdf>.

Mao, et al., "Capillary electrophoresis for the analysis fo glycosaminioglycans and glycosaminoglycan-derived oligosaccharides" Biomedical Chromatography, vol. 16, pp. 77-94 (2002).

Yamada et al., "Isolation of hte Porcine Heparin Testrasaccharides with Glucuronate 2-O—Sulfate" The Journal of Biological Cheminstry, vol. 270, No. 15, pp. 8696-8705 (1995).

Apsner et al., "Dalteparin-induced alopecia in hemodialysis patients: reversal by regional cirate anticoagulate as an example" Blood, vol. 97(9) pp. 2914-2915 (2001).

Bassas P et al., "Anticoagulation and Antiplatelet Therapy in Dermatology", ACTAS Dermosifiliograficas, vol. 100, No. 1, pp. 7-16 (2009).

Chu et al., "M-ONC 402, a novel low molecular weight heparin (LMWH) interacts with heparin-binding proteins and inhibits metastatic seeding of tumor cells in mice", Proceedings of the American Association for Cancer Research Annual Meeting, vol. 50 p. 1210 (2009).

De Lorenzo Ferruccio et al: "The role of anticoagulation in cancer patients: Facts and figures" Anti-Cancer Agents in Medicinal Chemistry, vol. 6, No. 6, pp. 579-587 (2006).

Derbyshire et al., "Anti-tumor and Anti-angiogenic effects in Mice of Heparin Conjugated to Angiostatic Steriods" Int. J. Cancer vol. 63 pp. 694-701 (1995).

Diaz-Montero et al., "Increased circulating myeloid-derived suppressor cells correlate with clinical cancer stage, mestastatic tumor burden, and doxorubicin-cyclophosphamide chemotherapy", Cancer Immunology Immunotherapy, vol. 58, No. 1 pp. 49-59 (2009).

Extended European Search Report from European Application No. 11769624.5 dated Jun. 26, 2013.

Extended European Search Report from European Application No., 11769718.5 dated Jul. 12, 2013.

Ferro Vito et al: "PI-88 and novel heparan sulfate mimetics inhibit angiogenesis" Seminars in Thrombosis and Hemostasis, vol. 33, No. 5, pp. 557-562 (2007).

Gabrilovich Dmitry I et al: "Myeloid-derived suppressor cells as regulators of the immune system" Nature Reviews Immunology, vol. 9, No. 3, pp. 162-174 (2009).

Gerotziafas G T et al: "Clinical studies with anticoagulants to improve survival in cancer patients" Pathophysiology of Haemostasis and Thrombosis 2008 S. Karger AG CHE LNKD—DOI:10.1159/000175158, vol. 36, No. 3-4, pp. 204-211 (2008).

He Zhou et al., "M-ONC 402-a non anticoagulant low molecular weight heparin inhibits tumor metastasisHe", Proceedings of the American Association for Cancer Research Annual Meeting, p. 69 (2009).

International Preliminary Report of Patentability and Written Opinion from International Application Serial No. PCT/US2008/082224 mailed Feb. 4, 2010.

International Search Report for PCT/US2011/32771 Nov. 23, 2011.

International Search Report including Written Opinion for PCT/US2011/040470 mailed Oct. 16, 2012.

(56) References Cited

OTHER PUBLICATIONS

Kondo et al., "Favorable Prognosis of Renal Cell Carcinoma with Increased Expression of Chemokines Associated with a Th1-type Immune Response," Cancer Science, 2006, vol. 97, Iss. 8, pp. 780-786.
Matsumoto et al., "Granulocyte-colony Stimulating Factor-producing Esophageal Carcinoma: Serum Level as a Marker for Monitoring the Effects of Treatment," International Journal of Clinical Oncology, 2000, vol. 5, Iss. 5, pp. 328-333.
Mousa Shaker A: "Role of current and emerging antithrombotics in thrombosis and cancer" Drugs of Today, vol. 42, No. 5, pp. 331-350 (2006).
Ostrand-Rosenberg Suzanne et al: "Myeloid-Derived Suppressor Cells: Linking Inflammation and Cancer" Journal of Immunology, vol. 182, No. 8, pp. 4499-4506 (2009).
Riedel et al, "Serum Levels of Matrix Metalloproteinase-2 and -9 in Patients with Head and Neck Squamous Cell Carcinoma," Anticancer Research, 2000, vol. 20, pp. 3045-3050.
Wang et al., "Enoxaparin-induced alopecia in patients with cerebral venous thrombosis", Journal of Clinical Pharmacy and Therapeutics, vol. 31, No. 5, pp. 513-517 (2006).
Washimi et al., "Measurement of plasma matrix methalloproteinase-9 in diagnosing metastatic bone tumors and evaluating the therapeutic effect," 62nd Proceedings of the Japanese Cancer Association, 2003, p. 48, 3445-PA.
Addison, et al., "The CXC Chemokine, Monokine Induced by Interferon-gamma, Inhibits Non-Small Cell Lung Carcinoma Tumor Growth and Metastasis" Human Gene Therapy, 11:247-261 (2000).
Avci et al., "Synthetic Oligosaccharides as Heparin-Mimetics Displaying Anticoagulant Properties" Current Pharm. Design, 9:2323-2335 (2003).
Beccati et al., "Identification of a novel structure in heparin generated by potassium permanganate oxidation" Carbohydrate Polymers, 82:699-705 (2010).
Beyer, et al., "Composition of OSCS-contaminated heparin occurring in 2008 in batches on the German market" European Journal of Pharmaceutical Sciences, 40:297-304 (2010).
Cui et al., "Structure Analysis of Polysaccharides" Food Carbohydrates: Chemistry, Physical Properties and Applications (2005).
Gerotziafas et al., "Effect of the anti-factor Xa and anti-factor IIa activities of low-molecular-weight heparins upon the phases of thrombin generation" Journal of Thrombosis and Haemostasis, 5:955-962 (2007).
Gray et al., "Heparin and Low-molecular-weight heparin" Thromb. Haemost vol. 99, pp. 807-818 (2008).
Halsall et al., "Oxidation of Carbohydrate by the Periodate Ion" Journal of Chemical Society, 172:1427-1432 (1947).
Hilbe, et al., "CD133 positive endothelial progenitor cells contribute to the tumour vasculature in non-small cell lung cancer" J Clin Pathol, 57:965-969 (2004).
International Preliminary Report of Patentability and Written Opinion from International Application Serial No. PCT/US2010/031480 mailed Oct. 18, 2011.
International Prelimnary Report of Patentability and Written Opinion from International Application Serial No. PCT/US2011/032581 mailed Oct. 16, 2012.
International Preliminary Report of Patentability and Written Opinion from International Application Serial No. PCT/US2011/032771 mailed Oct. 16, 2012.
International Search Report for PCT/US2008/082224 mailing date May 20, 2009.
International Search Report for PCT/US2010/031480 mailing date Sep. 27, 2010.
International Search Report for PCT/US2011/032581 mailing date Jul. 5, 2011.
International Search Report for PCT/US2014/039538 mailing date Oct. 1, 2014.
International Search Report for PCT/US2014/039542 mailing date Oct. 1, 2014.
Kragh, et al., "Non-anti-coagulant heparins: A promising approach for prevention of tumor metastasis (Review)" International Journal of Oncology, 27:1159-1167 (2005).
Lifespan, "Low Molecular Weight Heparin (LMWH) ELISA Kit for Buffer/Urine Samples" Mar. 8, 2013.
Lolkema, et al., "Abstract LB-43:M402, a novel heparin sulphate mimetic, synergizes with gemcitabine to improve survival and reduce metastasis and epithelial-to-mesenchymal transition (EMT) in a genetically engineered mouse model for pancreatic cancer" Cancer Research, 70(8 Suppl): Abstract LB-43 (2010).
Natori, et al., "G-CSF stimulates angiogenesis and promotes tumor growth: potential contribution of bone marrow-derived endothelial progenitor cells" Biochemical and Biophysical Research Communications, 297:1058-1061 (2002).
Sakuma et al., "Particulate Phase of Cellulose Cigarrette Smoke" Agric. Biol. Chem., 44(3):555-561 (1980).
Yamashita, et al., "Immunoreactive Hepatocyte Growth Factor Is a Strong and Independent Predictor of Recurrence and Survival in Human Breast Cancer" Cancer Research, 54:1630-1633 (1994).
Yao, et al., "Multiple signaling pathways involved in activation of matrix metalloproteinase-9 (MMP-9) by heregulin-beta1 in human breast cancer cells" Oncogene, 20:8066-8074 (2001).
Zea, et al., "Arginase-Producing Myeloid Suppressor Cells in Renal Cell Carcinoma Patients: A Mechanism of Tumor Evasion" Cancer Res., 65(8):3044-3048 (2005).
Zhou, et al., "Abstract #281: M-ONC 402-a non anticoagulant low molecular weight heparin inhibits tumor metastasis" Cancer Research, 69:Abstract 281 (2009).
Chinese Search Report from Chinese Application No. 201180019382.7 dated Jun. 7, 2014.
Ansel, H.C., Allen, Jr., L.V., Popovich, N.G. (1999) Pharmaceutical Dosage Forms and Drug Delivery Systems, published by Lippincott Williams & Wilkins, p. 48-53 and 120-128.
Gradishar, W.J. (2006) Albumin-bound paclitaxel: a next-generation taxane. Expert Opinion in Pharmacotherapy, vol. 7, No. 8, p. 1041-1053.
Kennett, E.C., Davies, M.J. (2009) Glycosaminoglycans are fragmented by hydroxyl, carbonate, and nitrogen dioxide radicals in a site selective manner: implications for peroxynitrite-mediated damage at sites of inflammation. Free Radical Biology & Medicine, vol. 47, p. 389-400.
Koliopanos, A., Friess, H., Kleef, J., Shi, X., Liao, Q., Peeker, I., Vlodaysky, I., Zimmermann, A., Buchler, M.W. (2001) Heparanase Expression in Primary and Metastatic Pancreatic Cancer. Cancer Research, vol. 61, p. 4655-4659.
Linhardt, R.J., Gunay, N.S. (1999) Production and Chemical Processing of Low Molecular Weight Heparins. Seminars in Thrombosis and Hemostasis, vol. 25, suppl. 3, p. 5-16.
Safran, H., Dipetrillo, T., Iannitti, D., Quirk, D., Akerman, P., Gruff, D., Cioffi, W., Shah, S., Ramdin, N., Rich, T. (2002) International Journal of Radiation Oncology Biology Physics, vol. 54, No. 1, p. 137-141.
"Fragmin" by RxList: The Internet Drug Index. Retrieved on [Aug. 19, 2014] [online]. Retrieved from the internet at <http://www.rxlist.com/fragmin-drug.htm>.
Casu et al., "Chemical Derivatization as a Strategy to Study Structure-Activity Relationships of Glycosaminoglycans", Seminars in Thrombosis and Hemostasis, col. 28, No. 4, pp. 335-342 (2002).
Casu et al., "Non-Anticoagulant Heparins and Inhibition of Cancer", Pathophysiol Haemost Thromb., vol. 36, pp. 195-203 (2007).
Casu et al., "Retention of Antilipemic Activity by Periodate-oxidized Non-anticoagulant Heparins", Arseneimittel Forschung/Drug Res. vol. 36 (1), No. 4, pp. 637-642 (1986).
Casu et al., "Short Heparin Sequences Spaced by Glycol-Split Uronate Residues Are Antagonists of Fibroblast Growth Factor 2 and Angiogenesis Inhibitors", Biochemistry, vol. 41, pp. 10519-10528 (2002).
Casu et al., "Undersulfated and Glycol-Split Heparins Endowed with Antiangiogenic Activity", J. Med. Chem., vol. 47, pp. 838-848 (2004).
Fransson et al., "Relationship between anticoagulant activity of heparin and susceptibility to periodate oxidation", Department of Physiological Chemsitry, vol. 97, No. 1, pp. 119-123 (1979).

(56) References Cited

OTHER PUBLICATIONS

Hrivocíni, et al., "Active Conformation of Glycosaminoglycans. NMR Determination of the Conformation of Heparin Sequences Complexed with Antithrombin and Fibroblast Growth Factors in Solution", Seminars in Thrombosis and Hemostasis, vol. 28, No. 4, pp. 325-333 (2002).

Icli et al., "Low moelecular weight heparin (LMWH) increase the efficacy of cisplatinum plus gemcitabine combination in advanced pancreatic cancer", J. Surg Oncol., vol. 95 (6), pp. 507-512 (2007) Abstract Only.

International Preliminary Report on Patentability for PCT/US2008/082223 filed Nov. 3, 2008.

International Search Report for PCT/US2008/082223 mailing date Jan. 28, 2009.

International Search Report for PCT/US2011/32581 date Jul. 5, 2011.

Kragh et al., "Non-anti-coagulant heparin inhibits metastasis but not primary tumor growth", Oncology Reports, vol. 14, pp. 99-104 (2005).

Mascellani et al., "Structure and Contribution to the heparin cofactor II-mediated inhibition of thrombin of naturally oversulphated sequences of dermatan sulphate" Biochem. J. vol. 296 pp. 639-648 (1993).

Naggi et al., "Modulation of the Heparanase-inhibiting Activity of Heparin through Selective Desulfation, Graded N-Acetylation, and Glycol Splitting", The Journal of Biological Chemistry, vol. 280, No. 13, pp. 12103-12113 (2005).

Peters et al., "Randomized comparison of a novel anticoagulant, vasoflux, and heparin as adjunctive therapy to streptokinase for acute myocardial infarction(vasoflux international trial for acute myocardial infarction lysis)", American Heart Journal., vol. 142 (2), pp. 237-243 (2001).

Pisano et al., "Undersulfated, low-molecular-weight glycol-split heparin as an antiangiogenic VEGFantagonist" Glycobiology, vol. 15, No. 2, pp. 1C-6C. (2005).

Ritchie et al., "A chemically modified heparin, inhibits myeloma growth and angiogenisis via disruption of the heparanase/syndecan-1 axis", Clin Can Res, pp. 1382-1393 (2011).

Sasisekharan et al., "Roles of Heparin-Sulphate Glycosaminoglycans in Cancer", Nature Reviews, vol. 2, pp. 521-528 (2002).

Spickler et al., "Clinical evaluation of the pharmacology, and safety of vasoflux[trademark symbol], a novel antithrombotic", Abstracts from the 70th scientific sessions, Nov. 9-12, 1997.

Weitz et al., "Vasoflux, a new anticoagulant with a novel mechanism of action", circ.ahajournals.org, pp. 682-689 (1999).

Written Opinion of the International Seaching Authority for PCT/US2011/32851 mailing date Jul. 5, 2011.

Written Opinion of the International Seraching Authority for PCT/US2008/082223.

Yang et al., "Targeting heparanase as a therapy for multiplemyeloma", Abstract # 257, Apr. 18, 2009.

Concentration Of $^3$H-MONC 402 Equivalents
In Tumor Of 4T1 Tumor-Bearing Female Balb/c Mice
Following A Single Subcutaneous Dose Of $^3$H-MONC 402 At 30 mg/kg

TISSUE TARGETING

CLAIM OF PRIORITY

This application is a national stage application under 35 U.S.C. §371 of PCT Application No. PCT/US2011/032771, filed Apr. 15, 2011, which claims priority to U.S. Application Ser. No. 61/325,146, filed Apr. 16, 2010. The disclosure of the prior application is considered part of (and is incorporated by reference herein) the disclosure of this application.

BACKGROUND OF THE INVENTION

Many anti-cancer agents attack cancer cells and normal cells alike. Therapeutic approaches to selectively target cancer tissues while minimizing toxic effects against normal tissues are therefore an important pursuit.

SUMMARY OF THE INVENTION

The invention is based, at least in part, on the discovery that a low molecular weight heparin described herein (e.g., a LMWH lacking substantial anticoagulant activity, e.g., M402) conjugated to a heterologous agent exhibited selective accumulation at the site of a primary tumor when administered to an experimental animal. Accordingly, the invention features, inter alia, methods to deliver and target an agent, e.g., a therapeutic or imaging agent, to a tumor site in a subject. Also included are related methods to deliver and target an agent, e.g., a therapeutic or imaging agent, to a site of inflammation, fibrosis or infection in a subject.

A "conjugate" as used herein, is a composition comprising a LMWH described herein linked to a heterologous active agent, such that the linkage remains substantially intact in the body of a subject after administration at least until the conjugate is targeted to a specified site (such as a tumor site). The LMWH and heterologous agent may be linked (e.g., covalently coupled) directly or via a linker or spacer. The linkage may be stable or cleavable (e.g., as in a prodrug) after targeting to the tumor site.

A "linker" or "spacer as used herein, may be any molecule that would be recognized and understood by a skilled artisan. These molecules may include moieties that are homo-bifunctional or hetero-bifunctional. In general, homo-bifunctional moieties include identical reactive groups while hetero-bifunctional moieties include non-identical reactive groups. These reactive groups can be chosen from any commonly accepted functional groups that are associated with linking or cross-linking biologically relevant molecules (e.g., hydrazides, N-hydrosuccinimides or dimethyl suberimidates). Molecules used as a linker and/or spacer may include a number of classes or compounds including polymers (e.g., a PEG polymer, polyacrylamide and other biologically compatible polymers), dyes and other compounds known to be useful in the linking and cross-linking of biologically relevant molecules (e.g., LMWHs).

"Targeting" of an agent to a tissue site with a conjugate described herein means that the agent is delivered to the site at a rate, and/or in an amount, and/or for a time greater than the agent would be delivered to the site if it were not conjugated as described herein.

As used herein, the term "subject" is intended to denote a human or non-human mammal, including, but not limited to, companion animals and experimental animals, such as a dog, cat, horse, cow, pig, sheep, goat, rabbit, guinea pig, primate, rat and mouse.

DETAILED DESCRIPTION

Figure 1:
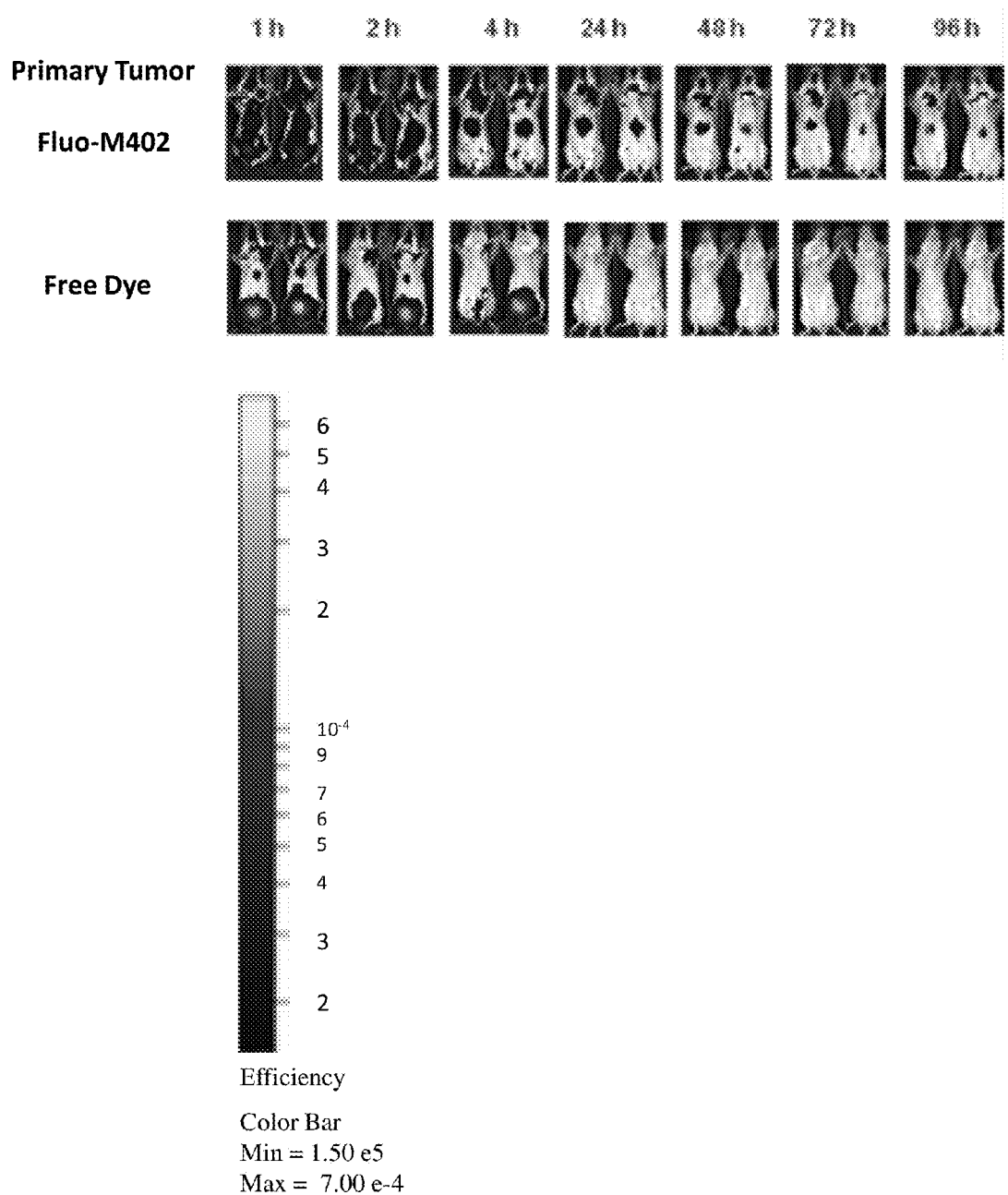
FIG. 1 shows the distribution of fluo-M402 (upper panels) and free dye (lower panels) in tumor-bearing mice.

Biodistribution studies indicated that M402 accumulates and persists in a tumor site, showing that M402 can be used to target a heterologous agent to a tumor site. Such targeting is useful, e.g., for one or more of: to preferentially deliver the agent to a target tumor site; to increase the half life of the agent compared to a non-targeted agent; to provide a slower release of the agent into the bloodstream compared to a non-targeted agent; to decrease the effective dose of the agent compared to a non-targeted agent; to lower a subject's resistance to the agent compared to a non-targeted agent.

Targeting Moiety

A LMWH described herein can be used to target a heterologous agent (e.g., a therapeutic or imaging agent) to a tumor site. Such a LMWH can have one or more of the following features: anti-Xa activity less than 50 IU/mg, 20 IU/mg, 10 IU/mg, 5 IU/mg or less; glycol split uronic acid residues (e.g., less than 50%, 40%, 30%, 20% glycol split uronic acid residues); no more than 3 glycol split uronic acid residues ($U_G$) per polysaccharide chain; greater than 40% $U_{2S}H_{NS,6S}$ disaccharide residues; degree of desulfation less than 40%; one or more polysaccharide chains have a 4,5-unsaturation of a non-reducing end uronic acid residue; one or more polysaccharide chains have a 2,5-anhydromannitol residue at the reducing end; weight average molecular weight of between 3,500 and 8,000 Da, e.g., between 4,000 and 8,000 Da; and a molecular weight distribution described herein.

Examples of targeting agents described herein include polysaccharide preparations that include chains that include the following:

wherein U indicates a uronic acid residue and H indicates a hexosamine residue, wherein m and n are integers such that m=6-18, and n=1-4, w=–2OS or –2OH, x=—NS or —NAc, y=–3OS or –3OH, z=–6OS or –6OH, and

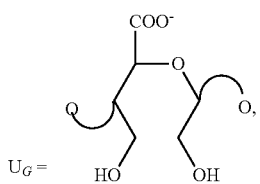

wherein the symbol indicates that the units marked m and n are distributed along the polysaccharide chain and are not necessarily in sequence.

For example, the following polysaccharide chain is encompassed by this embodiment:

$$[U_G\text{-}H_{x,y,z}]\text{-}[U_w\text{-}H_{x,y,z}]\text{-}[U_G\text{-}H_{x,y,z}]\text{-}[U_w\text{-}H_{x,y,z}]\text{-}[U_w\text{-}H_{x,y,z}]\text{-}[U_w\text{-}H_{x,y,z}]$$

In addition, each of w, x, y, and z can be the same or different for each occurrence of $[U_w\text{-}H_{x,y,z}]$, and each of x, y, and z can be the same or different for each occurrence of $[U_G\text{-}H_{x,y,z}]$. Each occurrence of U can independently be an iduronic acid (I) or a glucuronic acid (G).

The polysaccharide preparation can have anti-Xa activity and anti-IIa activity each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg; and anti-IIa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg); and $$[U_w\text{-}H_{x,y,z}]_m\text{-}[U_G\text{-}H_{x,y,z}]_n\text{-}[U_w\text{-}H_{x,y,z}]_o\text{-}[U_G\text{-}H_{x,y,z}]_p\text{-}[U_w\text{-}H_{x,y,z}]_q$$

wherein U indicates a uronic acid residue and H indicates a hexosamine residue, wherein m-q are integers such that: m=0-10, n=0-3, o=0-10, p=0-3, q=0-10, w=–2OS or –2OH, x=—NS or —NAc, y=–3OS or –3OH, z=–6OS or –6OH, and

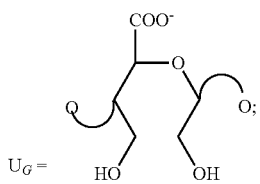

wherein w, x, y, and z are each the same or different on each unit marked m, n, o, p, or q. In some embodiments, the sum of n+p is less than or equal to 4 (e.g., less than or equal to 3, 2, 1, or 0). In some embodiments, the sum of n and p is 4, 3, 2 or 1. In some embodiments, the sum of m, o and q is between 4 and 18, e.g., 4-8, 4-9, 4-10, 4-11, 4-12, 4-13, 4-14, 4-15, 4-16 or 4-17. In some embodiments, the preparation has a weight average chain molecular weight between 3,500 and 7,000 Da, e.g., 4,300 and 7000 Da, 4,500 and 7,000 Da, 4,700 and 7,000 Da and 5,000 and 7,000 Da.

In addition, each of w, x, y, and z can be the same or different for each occurrence of $[U_w\text{-}H_{x,y,z}]$, and each of x, y, and z can be the same or different for each occurrence of $[U_G\text{-}H_{x,y,z}]$. Each occurrence of U can independently be an iduronic acid (I) or a glucuronic acid (G).

The polysaccharide preparation can have anti-Xa activity and anti-IIa activity each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg; and anti-IIa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg).

Anti-IIa Activity: Anti-IIa activity is calculated in International Units of anti-IIa activity per milligram using statistical methods for parallel line assays. The anti-IIa activity levels described herein are measured using the following principle.

Polysaccharide (PS)+ATIII→[PS·ATIII]

IIa

PS·ATIII→[PS·ATIII·IIa]+IIa(Excess)

IIa(Excess)+Substrate→Peptide+pNA(measured spectrophotometrically)

Anti-factor IIa activity is determined by the sample potentiating effect on antithrombin (ATIII) in the inhibition of thrombin. Thrombin excess can be indirectly spectrophotometrically measured. The anti-factor IIa activity can be measured, e.g., on a Diagnostica Stago analyzer or on an ACL Futura3 Coagulation system, with reagents from Chromogenix (S-2238 substrate, Thrombin (53 nkat/vial), and Anti-thrombin), or on any equivalent system. Analyzer response is calibrated using the 2nd International Standard for Low Molecular Weight Heparin.

Anti-Xa Activity: Anti-Xa activity of a preparation is calculated in International Units of anti-factor Xa activity per milligram using statistical methods for parallel line assays. The anti-factor Xa activity of preparations described herein is measured using the following principle:

PS+ATIII→[PS·ATIII]

FXa

PS·ATIII→[PS·ATIII·FXa]+FXa(Excess)

FXa(Excess)+Substrate→Peptide+pNA(measured spectrophotometrically)

The anti-factor Xa activity is determined by the sample potentiating effect on antithrombin (ATIII) in the inhibition of activated Factor Xa (FXa). Factor Xa excess can be indirectly spectrophotometrically measured. Anti-factor Xa activity can be measured, e.g., on a Diagnostica Stago analyzer with the Stachrom® Heparin Test kit, on an ACL Futura3 Coagulation system with the Coatest® Heparin Kit from Chromogenix, or on any equivalent system. Analyzer response can be calibrated using the NIBSC International Standard for Low Molecular Weight Heparin.

Molecular Weight and Chain Length: When weight average molecular weight of a preparation is determined, a weight average molecular weight of about 3500 to 8000 Da, about 3500 to 6300 Da, preferably about 4000 to 6000 Da, about 4200 to 5900, or about 4300 to 5800 Da, indicates that a significant number of chains in the polysaccharide preparation are of sufficient chain length. "Weight average molecular weight" as used herein refers to the weight average in daltons of chains of uronic acid/hexosamine disaccharide repeats. The presence of non-uronic acid and/or non-hexosamine building blocks are not included in determining the weight average molecular weight. Thus, the molecular weight of non-uronic acid and non-hexosamine building blocks within a chain or chains in the preparation should not be included in determining the weight average molecular weight. The weight average molecular weight ($M_w$) is calculated from the following equation: $M_w=\Sigma(c_i m_i)/\Sigma c_i$. The variable $c_i$ is the concentration of the polymer in slice i and $m_i$ is the molecular weight of the polymer in slice i. The summations are taken over a chromatographic peak, which contains many slices of data. A slice of data can be pictured as a vertical line on a plot of chromatographic peak versus time. The elution peak can therefore be divided into many slices. The weight average molecular weight calculation is average dependant on the summation of all slices of the concentration and molecular weight. The weight average molar weight can be measured, e.g., using the Wyatt Astra software or any appropriate software. The weight average molecular weights described herein are determined by high liquid chromatography with two columns in series, for example a TSK G3000 SWXL and a G2000 SWXL, coupled with a multi angle light scattering (MALS) detector and a refractometric detector in series. The eluent used is a 0.2 M sodium sulfate, pH 5.0, and a flow rate of 0.5 mL/min.

A determination of whether a polysaccharide preparation includes chains of sufficient chain length can be made, for example, by determining the average chain length of the chains in the preparation and/or by determining the weight average molecular weight of chains within the preparation. When average chain length is determined, an average chain length of about 5 to 22, e.g., about 7 to 18, typically about 7 to 14 or 8 to 13 disaccharide repeats, indicates that a significant number of chains in the preparation are of sufficient chain length.

"Average chain length" as used herein refers to the average chain length of uronic acid/hexosamine disaccharide repeats that occur within a chain. The presence of non-uronic acid and/or non-hexosamine building blocks (e.g., attached PEG moieties) are not included in determining the average chain length. Average chain length is determined by dividing the number average molecular weight (Mn) by the number average molecular weight for a disaccharide (500 Da).

Glycol Split Uronic Acids: A polysaccharide preparation described herein can include an opening of the glycoside ring, conventionally called reduction-oxidation (RO) derivatives. In these preparations, one or more glycoside rings having vicinyl diols that are opened, e.g., at the bond between C2 and C3, by means of an oxidation action, followed by a reduction. The compounds referred to herein will also be called "Glycol Split" derivatives. In a further embodiment of the invention described herein, the glycol split residues lend themselves to the subsequent functionalization. Therefore, the compounds may also bear equal or different groups, in place of the primary hydroxy groups deriving from glycol split, for example, aldehyde groups, methoxy groups, or oligosaccharide or peptide groups, ranging from a single saccharide or amino acid to more than one unit of length, e.g., 2 or 3 units.

In some embodiments, fewer than 50% of the uronic acid residues are glycol split uronic acid residues (e.g., less than 40%, 30%, 25%, or 20% of the uronic acid residues are glycol split uronic acid residues).

Reducing End Structures: In some instances, at least about 50% of the chains in a polysaccharide preparation described herein have a modified reducing end structure such as a 2,5-anhydromannose residue or a 2,5-anhydromannose that has been reduced to form an alcohol. In some embodiments, at least about 55%, 60%, 65%, 70%, 75%, 80%, 85%, 90%, or 95% of the chains in the preparation have a modified reducing end structure, such that the reducing end includes a 2,5-anhydromannose residue or a 2,5-anhydromannose that has been reduced to form an alcohol.

Polydispersity: The polydispersity of polysaccharide preparations provided herein is about 2 or less, e.g., 1.7 or less, e.g., about 1.7 or 1.6 to 1.2, about 1.4-1.5, and numbers in between.

The term "polydisperse" or "polydispersity" refers to the weight average molecular weight of a composition (Mw) divided by the number average molecular weight (Mn). The number average molecular weight (Mn) is calculated from the following equation: $Mn=\Sigma ci/(\Sigma ci/ml)$. The variable ci is the concentration of the polysaccharide in slice i and Mi is the molecular weight of the polysaccharide in slice i. The summations are taken over a chromatographic peak, which contains many slices of data. A slice of data can be pictured as a vertical line on a plot of chromatographic peak versus time. The elution peak can therefore be divided into many slices. The number average molecular weight is a calculation dependent on the molecular weight and concentration at each slice of data. Methods of determining weight average molecular weight are described above, and were used to determine polydispersity as well.

Methods of Making Polysaccharide Preparations Used as Targeting Agents Described Herein One method includes providing a precursor heparin preparation having an average molecular weight of greater than 7000 Da or a chain length of greater than 7 to 18 disaccharides, and processing the precursor heparin preparation (e.g., by enzymatic or chemical depolymerization, e.g., by nitrous acid depolymerization) to obtain a polysaccharide preparation having an average molecular weight of about 3000 to 7000 Da or an average chain length of about 7 to 18 disaccharides. For example, the precursor heparin preparation can be unfractionated heparin.

The precursor heparin preparation can be processed by a method comprising depolymerization (e.g., by nitrous acid treatment, hydrolysis, or enzymatic depolymerization) followed by a glycol split reaction. Nitrous acid depolymerization can be accomplished, e.g., by treating the precursor heparin preparation (e.g., UFH) with nitrous acid (e.g., about 0.02 to 0.04 M nitrous acid) at a pH of about 2 to 4 for a specified period of time (e.g., about 1 to 5 hours) at a temperature of about 10 to 30° C. The glycol split reaction involves periodate oxidation using periodate (e.g., about 0.05 M to 0.2 M sodium periodate) for about 10 to 20 hours at a temperature of about 0 to 10° C. In some embodiments, residual impurities such as salts or diethylene glycol (DEG) can be subsequently removed by a chromatographic method, e.g. gel filtration chromatography. Optionally, the oxidized preparation is then reduced by treatment with a reducing agent (e.g., about 0.5 to 2.0% (w/v) sodium borohydride) for about 0.5 to 3 hours at a pH of about 6.0 to 7.0 and a temperature of about 0 to 10° C.

A precursor heparin preparation can be processed using enzymatic digestion, chemical digestion or combinations thereof. Examples of chemical digestion include oxidative depolymerization, e.g., with $H_2O_2$ or $Cu^+$ and $H_2O_2$, deaminative cleavage, e.g., with isoamyl nitrite or nitrous acid, β-eliminative cleavage, e.g., with benzyl ester, and/or by alkaline treatment. Enzymatic digestion can include the use of one or more heparin degrading enzymes. For example, the heparin degrading enzyme(s) can be, e.g., one or more heparinase, heparin lyase, heparin sulfate glycoaminoglycan (HS-GAG) lyase, a lyase described as a glycoaminoglycan (GAG) lyase that can also degrade heparin. Preferably, the enzyme cleaves at one or more glycosidic linkages of unsulfated uronic acids.

Anti-Tumor Agents

The conjugates and methods described herein include use of an agent, e.g., an anti-tumor agent, which can be targeted to a tumor site in a subject. The methods and compositions are not limiting with regard to such agents that may be used.

In one embodiment, the agent is an imaging agent, e.g., a magnetic agent (e.g., for MRI), a fluorescent agent, a biologically active enzyme label, a radioisotope (e.g., a radioactive ion), a luminescent label, or a chromophore. A radioisotope can be an α-, β-, or γ-emitter, or an β- and γ-emitter. Radioisotopes useful as therapeutic agents include yttrium ($^{90}Y$), lutetium ($^{177}Lu$), actinium ($^{225}Ac$), praseodymium, astatine ($^{211}At$) rhenium ($^{186}Re$) bismuth ($^{212}Bi$ or $^{213}Bi$) and rhodium ($^{188}Rh$). Radioisotopes useful as labels, e.g., for use in diagnostics, include iodine ($^{131}I$ or $^{125}I$), indium ($^{111}In$) technetium ($^{99m}Tc$), phosphorus ($^{32}P$), carbon (.sup.14C), and tritium ($^{3}H$), In some embodiments, the agent is a therapeutic agent, e.g., a radioisotope (e.g., a radioisoptope described above), a cytotoxic agent, a tyrosine kinase inhibitor, a proteasome inhibitor, a protease inhibitor, an anti-angiogenic agent, an anti-metastatic agent, a steroid, a biologic immunomodulator, a monoclonal antibody, an antibody fragment, an aptamer, an siRNA, an antisense molecule, a fusion protein, a cytokine or chemokine, a cytokine or chemokine receptor, a bronchodialator, a statin, an anti-inflammatory agent, a microtubule inhibitor, a topoisomerase inhibitor, an antimetabolite, a protein synthesis and degradation inhibitor, a mitotic inhibitor, an alkylating agent, a platinating agent, an inhibitors of nucleic acid synthesis, a histone deacetylase and DNA methyltransferase inhibitor, a nitrogen mustard, a nitrosourea, an ethylenimine, an alkyl sulfonate, a triazene, a folate analog, a nucleoside analog, a ribnucleotide reductase inhibitor, a vinca alkaloid, a taxane, an epothilone, an intercalating agent, a signal transduction inhibitor, an apoptosis inducer, a cytokine, a chemokine, and a vaccine.

In one embodiment, the agent may be selected from small organic molecules, proteins, peptides, nucleic acids (e.g., gene therapy), antibodies, amino acids, lipids, polysaccharides, cell growth factors, and enzymes.

In one embodiment, the agent is cisplatin, cyclophosphamide, dacarbazine, methotrexate, fluorouracil, gemcitabine, capecitabine, hydroxyurea, topotecan, irinotecan, azacytidine, vorinostat, ixabepilone, bortezomib, a taxane (paclitaxel, docetaxel), cytochalasin B, gramicidin D, ethidium bromide, emetine, mitomycin, etoposide, tenoposide, vincristine, vinblastine, vinorelbine, colchicin, anthracyclines (doxorubicin and epirubicin) daunorubicin, dihydroxy anthracin dione, mitoxantrone, mithramycin, actinomycin D, adriamycin, 1-dehydrotestosterone, glucocorticoid, procaine, tetracaine, lidocaine, propranolol, puromycin, ricin, and maytansinoids, Gefitinib, Erlotinib, Lapatinib, Sorafenib, Sunitinib, Imatinib, Dasatinib, Nilotinib, temsirolimus, everolimus, rapamycin, Trastuzumab, Cetuximab, Panitumumab, Bevacizumab, Rituximab, Tositumomab.

Chemical Conjugation

Strategies are known for preparing small molecule-carbohydrate conjugates and polypeptide-carbohydrate conjugates (e.g., wherein the carbohydrate is a heparin-derived carbohydrate), directly or through a linker, e.g., as described in the following:

Wang et al. 2009. *Pharmaceutical Research* 785-793, describing conjugates of heparin and a chemotherapeutic agent (e.g., a taxane), including a paclitaxel-heparin conjugate;

Lee et al. (2001) *Circulation* 104:3116-3120, describing production of LMWH-Deoxycholic Acid (DOCA) by reacting activated DOCA with heparin in the cosolvent of dimethylformamide and water;

Cho et al. 2008. *Bioconjugate Chem.* 19(7):1346-1351, describing bonding of carboxyl groups of heparin with amine groups of aminated molecules;

Lee et al. 2008. *Int J Cancer* 124:2755-2765, describing conjugation of heparin to heterologous agents via amide formation.

U.S. Pat. No. 6,245,753 and U.S. Pat. No. 6,656,922, describing heparin conjugates with bile acids, sterols, alkanoic acids;

Chan et al. 1997. *J Biol Chem,* 272:22111-22117, describing heparin covalently linked to antithrombin though aldose termini;

Thorpe et al. 1993. *Cancer Res* 53.3000-3007, describing preparation of heparin-steroid conjugates.

Wang et al., 2009. *Bioorganic and Medicinal Chemistry Letters* 19:149-152, describing heparin conjugates through designed ester bonds;

US 2009/0149424, describing a composition wherein a bile acid is bonded to heparin through the 3-carbon of the bile acid, with an optional spacer, and heparin covalently bonded to a sulfonated moiety, such as a naphthalene trisulfonate residue;

Barzu et al. 1986. *Biochem J* 238:847-854, describing heparin conjugated to stoichiometric amounts of $Na^{125}I$;

Hatton et al. 1980. *Analytical Biochemistry* 106:417-426, describing methods to tritiate heparin samples;

U.S. Pat. No. 5,308,617, describing protein agents covalently conjugated via lysine residues or amino-terminal amines to a heparin fragment having a terminal 2,5-anhydro-D-mannose residue through the aldehyde group of such residue;

U.S. Pat. No. 7,517,856, describing bioconjugates between a sulfated polysaccharide and a bioactive polypeptide, wherein the bioactive polypeptide non-covalently associates with a sulfate group of the sulfated polysaccharide;

U.S. Pat. No. 7,417,021, describing conjugates of biopolymers such as heparins and a therapeutic agent, joined by a disulfide bond, with and without spacers;

U.S. Pat. No. 7,166,708, describing polysaccharide conjugates of an oxidation-sensitive substance.

Formulation and Administration

The conjugates described herein can be formulated as pharmaceutical compositions for medical imaging, diagnosis or treatment. Such compositions typically include appropriate pharmaceutically acceptable carriers (such as buffering agents and adjuvants) and, optionally, other therapeutic or diagnostic agents, using well known formulation protocols. Administration of the pharmaceutical compositions can be accomplished using an appropriate vehicle, e.g., injectable solutions. Administration can be, e.g., intravenously, subcutaneously, intra-muscularly, intra-peritoneally, or orally. The precise amount of the conjugate used in the pharmaceutical composition can be determined based on the nature of the condition to be treated, and the potency of the therapeutic agent used.

All references cited herein are incorporated herein by reference in their entirety.

EXAMPLES

Example 1

Conjugation of M402 with Fluorescent Dye and Radioactive Isotope

M402 conjugated to fluorescent dye was prepared by treating M402 with HiLyte Fluor™ 750 Hydrazide (AnaSpec, Fremont, Calif.) in the presence of a catalyst such as EDC at room temperature. The final product was isolated by salt-methanol precipitation.

M402 was conjugated to $^3$H by methods essentially as described by Hatton et al. 1980. *Analytical Biochemistry* 106: 417-426.

Example 2

Targeting of M402-Fluo Conjugate and M402-$^3$H Conjugate to Tumor Site

This example shows that M402 can be used to target a heterologous agent (e.g., an imaging or therapeutic agent) to a tumor site.

Figure 2:
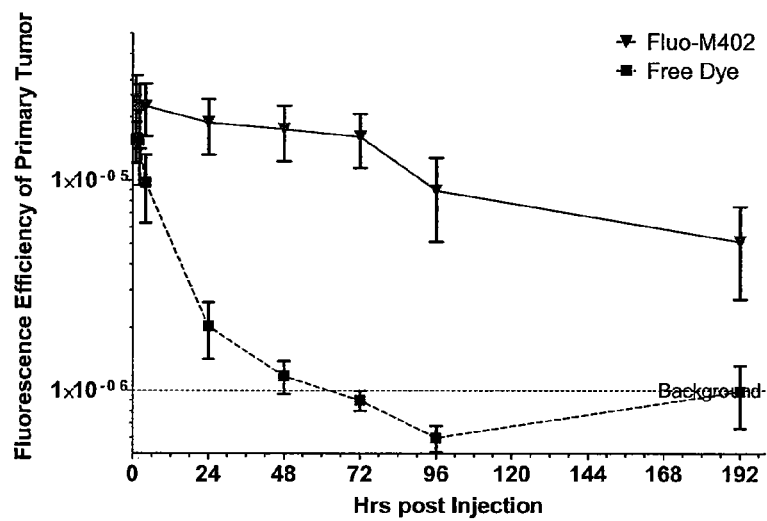
FIG. 2 is a graph showing a time course of the level of fluorescent signal in the primary tumor in mice injected with fluo-M402 or free dye.
Figure 3:
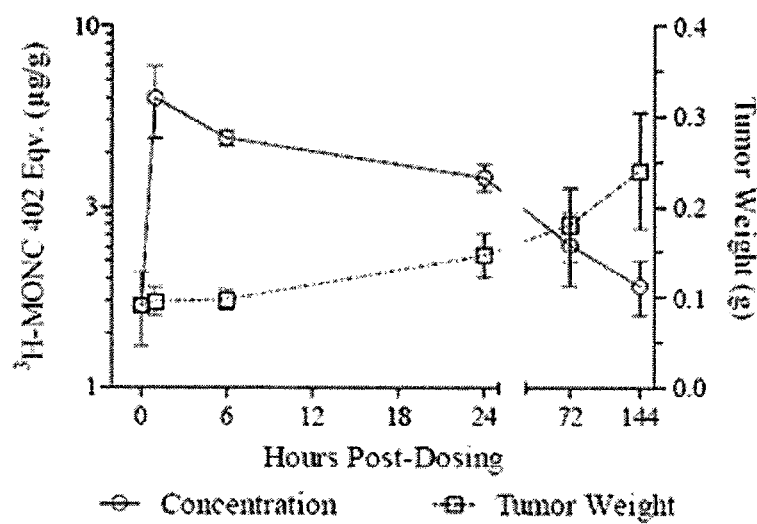
FIG. 3 is a graph showing the accumulation of titrated M402 at the tumor site in tumor-bearing mice following a single sc dose of $^3$H-M402.

M402 was labeled with a HiLyte Fluor™ 750 dye to enable visualization of the biodistribution of M402. Normal or tumor-bearing mice were treated with a single dose of fluorescent-labeled M402 or with free HiLyte Fluor™ 750 dye and monitored at different time points by fluorescent imaging using an IVIS Lumina instrument. The distribution of fluorescent M402 in non-tumor bearing mice was observed in the liver and bladder within 1 hour after injection, consistent with rapid clearance of LMWH through the kidney and liver. However, in tumor-bearing animals, M402-associated fluorescent signals were readily detectable in the area of the first mammary fat pad, where the 4T1 cells were implanted, in addition to the bladder and liver (FIG. 1, upper panels). Importantly and surprisingly, fluorescent signal in the primary tumor area persisted up to 192 hours (8 days) after a single injection (FIG. 2). The distribution was confirmed by ex vivo imaging of isolated tumor as well as by biodistribution studies performed with $^3$H-labeled M402. As shown in FIG. 3, tritiated M402 accumulated at the tumor site within 1 hour, and persisted though longer than 72 hours (circles). In contrast, in mice injected with free dye, the fluorescent signal accumulated mostly in the bladder within the first 4 hours, and was not detectable 24 hours after injection (FIG. 1, lower panels). Histological examination of the primary tumors indicated that M402 colocalized with fibrotic bands around the tumor tissue as well as around individual tumor cells.

The accumulation of the fluorescent signal in the tumor area, including in fibrotic bands, was interesting and unexpected. While not bound by theory, M402 may be targeting to the extracellular matrix (ECM) in fibrotic bands in the tumor tissue, e.g., via M402-binding growth factors found in such ECM and/or to areas rich in growth factors, cytokines or chemokines that contain heparin-binding motifs. Accordingly, targeting to fibrotic and inflammatory lesions, and to sites of infection, is also contemplated by the invention.

Example 3

Multiple Injections of Fluo-M402

This example shows a 25 day experiment of mice injected with a 7 day daily Fluo-M402 regiment and the results of that experiment.

Figure 4:
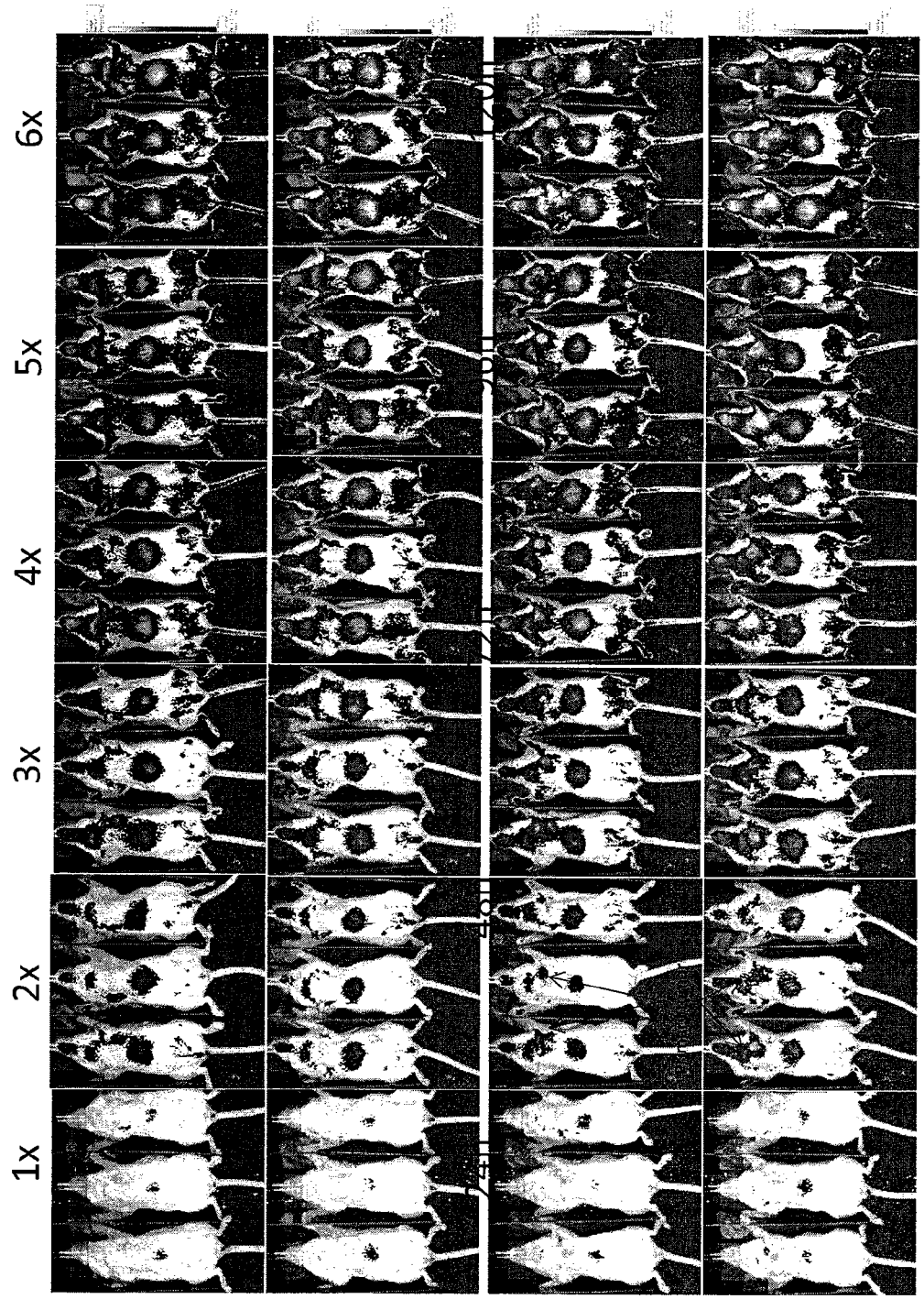
FIG. 4 shows the distribution of fluo-M402 in tumor-bearing mice and non-tumor bearing mice 24 hr after a single daily sc dose of fluo-M402 for 6 consecutive days.
Figure 5:
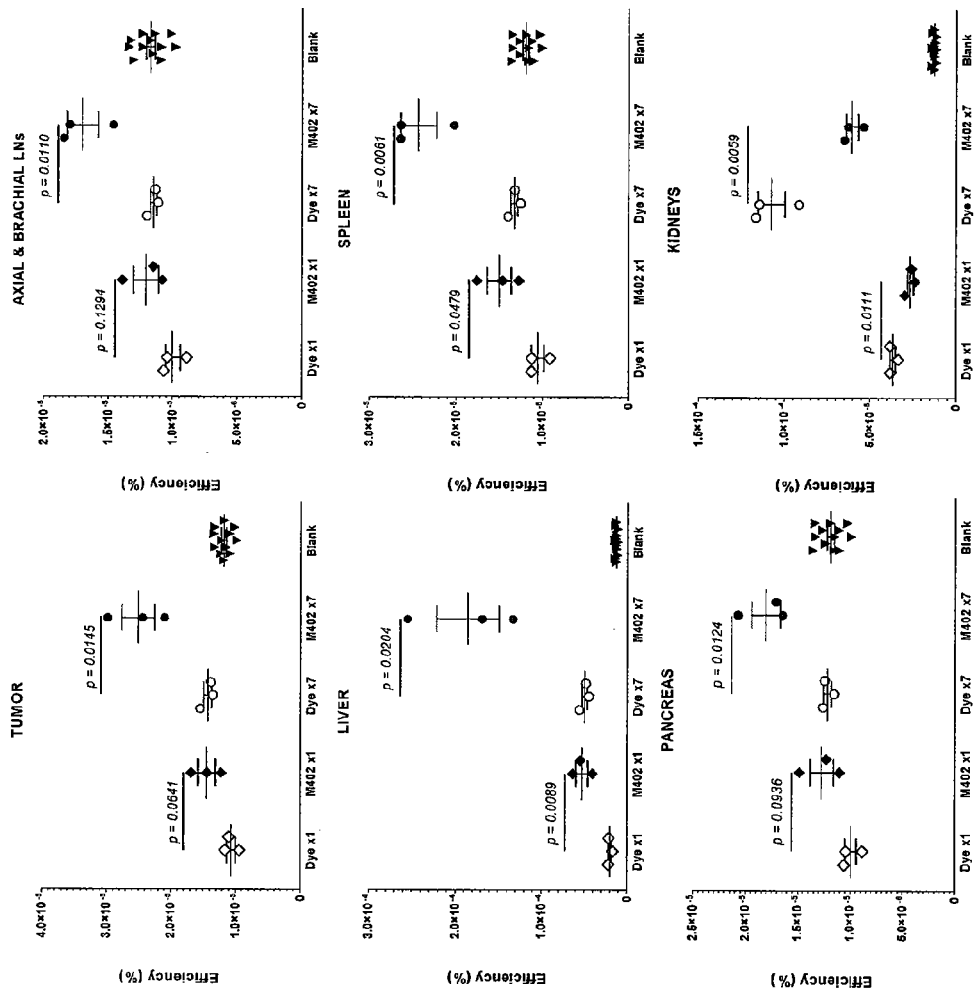
FIG. 5 represents graphs showing the accumulation of fluo-M402 in a number of different tissues (e.g., tumor, liver, spleen) 24 h after the last of 7 daily injections of fluo-M402 for 7 consecutive days.
Figure 6:
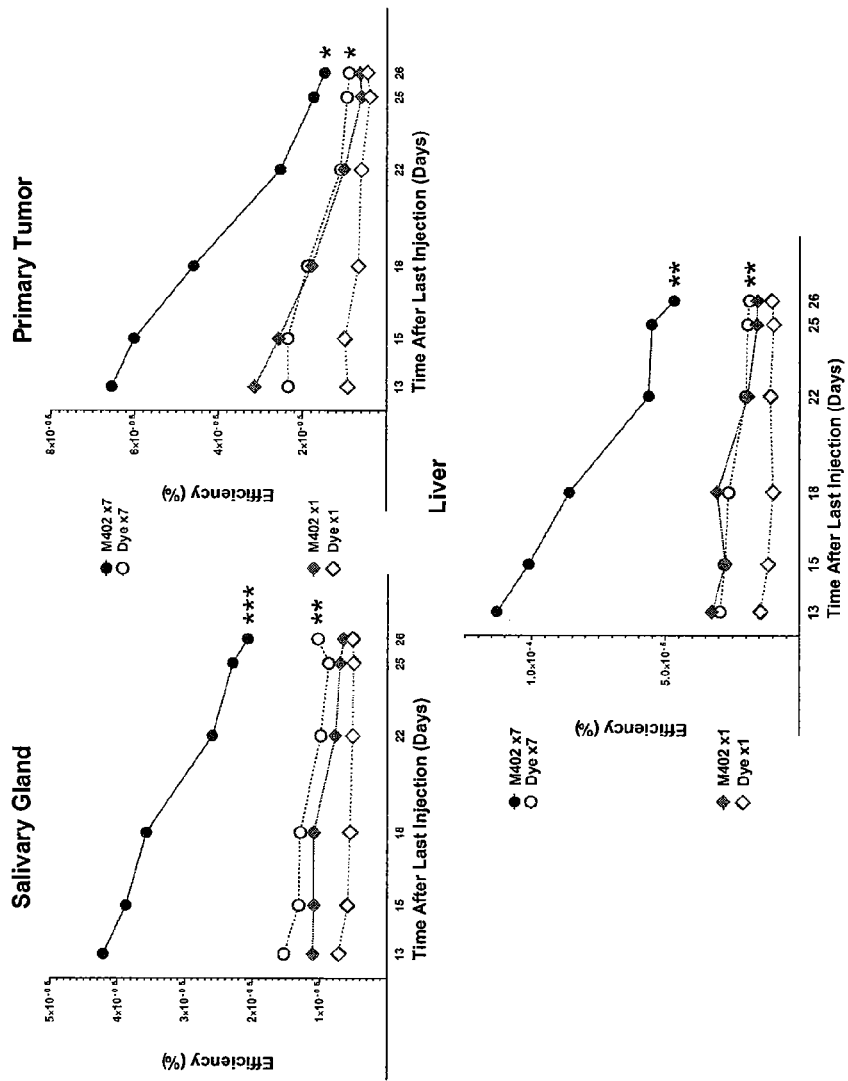
FIG. 6 represents graphs showing a time course of the level of fluorescent signal in the primary tumor, salivary glands and liver in mice treated with a single daily injection of fluo-M402 for 7 consecutive days.

As described in Example 1, M402 was labeled with a HiLyte Fluor™ 750 dye to enable visualization of the biodistribution of M402. Normal or tumor-bearing mice were treated with a single daily dose of fluorescent-labeled M402 on days 5-11. The distribution of fluorescent M402 in tumor-bearing non-tumor bearing mice was observed within 24 hours after the daily injection on days 6-12. M402-associated fluorescent signals were readily detectable in the area of the bladder, liver and first mammary fat pad (FIG. 4). It was also found that multiple doses of Fluo-M402 resulted in specific accumulation in different tissues such as the primary tumor, the axial and brachial LNs, the liver, the spleen, the pancreas and the kidneys (FIG. 5). Fluorescent signal in the Axial and brachial LNs, liver, spleen, pancreas, kidneys and primary tumor tissues show a more pronounced accumulation upon several injections when compared to a single injection and when compared with injections of the dye alone. Lastly, it was found that the fluorescent signal in the salivary glands, the liver and the primary tumor persisted at least 2-3 weeks following the multiple injection treatment with Fluo-M402 (FIG. 6).

We claim:

1. A method of targeting a therapeutic or imaging agent to a tumor tissue of a patient, the method comprising (a) identifying a patient with a tumor tissue, wherein the patient is in need of administration of a therapeutic or imaging agent to treat or image the tumor; (b) providing a conjugate of the therapeutic or imaging agent and a polysaccharide preparation; and (c) administering the conjugate to the patient, wherein the polysaccharide preparation targets the conjugate to the tumor tissue, and wherein the polysaccharide preparation has the following characteristics:

a weight average chain molecular weight between 3,500 and 8,000 Da;

anti-Xa activity and anti-IIa activity each less than 50 IU/mg; and greater than 5% and less than 50% glycol split uronic acid residues;

and wherein the polysaccharide preparation comprises polysaccharides of the Formula I:

$$[U_w\text{---}H_{x,y,z}]_m\text{~}[U_G\text{---}H_{x,y,z}]_n \qquad (I)$$

wherein each occurrence of U indicates a uronic acid residue and each occurrence of H indicates a hexosamine residue;

wherein m and n are integers such that
m=4-16, and
n=1-4;

each of w, x, y and z can independently be the same or different for each occurrence of $[U_w\text{---}H_{x,y,z}]$ and each of x, y and z can independently be the same or different for each occurrence of $[U_G\text{---}H_{x,y,z}]$, wherein w=-2OS or -2OH;
x=-NS or -NAc;
y=-3OS or -3OH;
z=-6OS or -6OH; and

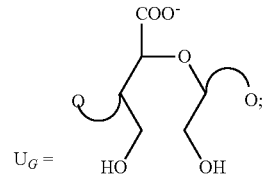

$U_G =$ wherein the symbol ~ indicates that the units marked m and n are distributed along the polysaccharide chain and are not necessarily in sequence to thereby target the agent to the tumor tissue.

2. The method of claim 1, wherein the agent is selected from a radioactive agent, a fluorescent agent, a cytotoxic agent, a tyrosine kinase inhibitor, a proteasome inhibitor, a protease inhibitor, an anti-angiogenic agent, an anti-metastatic agent, a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent, a microtubule inhibitor, a topoisomerase inhibitor, an antimetabolite, a protein synthesis and degradation inhibitor, a mitotic inhibitor, an alkylating agent, a platinating agent, an inhibitor of nucleic acid synthesis, a histone deacetylase and DNA methyltransferase inhibitor, a nitrogen mustard, a nitrosourea, an ethylenimine, an alkyl sulfonate, a triazene, a folate analog, a nucleoside analog, a ribnucleotide reductase inhibitor, a vinca alkaloid, a taxane, an epothilone, an intercalating agent, a signal transduction inhibitor, an apoptosis inducer, a cytokine, a chemokine, and a vaccine.

3. The method of claim 1, wherein the agent is selected from the group consisting of: cisplatin, cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes, cytochalasin B, gramicidin D, ethidium bromide, emetine, mitomycin, etoposide, tenoposide, vincristine, vinblastine, vinorelbine, colchicin, anthracyclines daunorubicin, dihydroxy anthracin dione, mitoxantrone, mithramycin, actinomycin D, adriamycin, 1-dehydrotestosterone, glucocorticoid, procaine, tetracaine, lidocaine, propranolol, puromycin, ricin, Ilmaytansinoids, Gefitinib, Erlotinib, Lapatinib, Sorafenib, Sunitinib, Imatinib, Dasatinib, Nilotinib, temsirolimus, everolimus, rapamycin, Trastuzumab, Cetuximab, Panitumumab, Bevacizumab, Rituximab, and Tositumomab.

4. The method of claim 1, wherein the tumor is a solid tumor.

5. The method of claim 1, wherein the tumor is a primary cancer site or a metastasis site.

6. The method of claim 1, further comprising one or more of the following steps: biopsing the tumor tissue, imaging the tumor tissue, and evaluating the effect of the administration on the tumor tissue.

7. The method of claim 1, wherein the conjugate is administered intravenously, subcutaneously, intra-muscularly, intra-peritoneally, or orally.

8. A method of treating a subject, the method comprising: (a) identifying a subject who has a tumor, and (b) administering to the subject a therapeutically effective amount of a pharmaceutical composition comprising a conjugate of an anti-tumor agent and a polysaccharide preparation; and (c) administering the conjugate to the patient, wherein the polysaccharide preparation has the following characteristics: has the following characteristics:
 a weight average chain molecular weight between 3,500 and 8,000 Da;
 anti-Xa activity and anti-IIa activity each less than 50 IU/mg; and
 greater than 5% and less than 50% glycol split uronic acid residues;
 and wherein the polysaccharide preparation comprises polysaccharides of the Formula I:

$$[U_w\text{—}H_{x,y,z}]_m\text{~}[U_{G'}\text{—}H_{x,y,z}]_n \quad (I)$$

wherein each occurrence of U indicates a uronic acid residue and each occurrence of H indicates a hexosamine residue;
wherein m and n are integers such that m =4-16, and n =1-4;
each of w, x, y and z can independently be the same or different for each occurrence of $[U_w\text{—}H_{x,y,z}]$ and each of x, y and z can independently be the same or different for each occurrence of $[U_w\text{—}H_{x,y,z}]$, wherein
w =-2OS or -2OH;
x =-NS or -NAc;
y =-3OS or -3OH;
z =-6OS or -6OH;
and

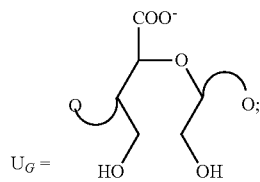

$U_G =$ wherein the symbol ~ indicates that the units marked m and n are distributed along the polysaccharide chain and are not necessarily in sequence.

9. The method of claim 8, wherein the anti-tumor agent is selected from a radioactive agent, a cytotoxic agent, a tyrosine kinase inhibitor, a proteasome inhibitor, a protease inhibitor, an anti-angiogenic agent, an anti-metastatic agent, a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent, a microtubule inhibitor, a topoisomerase inhibitor, an antimetabolite, a protein synthesis and degradation inhibitor, a mitotic inhibitor, an alkylating agent, a platinating agent, an inhibitor of nucleic acid synthesis, a histone deacetylase and DNA methyltransferase inhibitor, a nitrogen mustard, a nitrosourea, an ethylenimine, an alkyl sulfonate, a triazene, a folate analog, a nucleoside analog, a ribnucleotide reductase inhibitor, a vinca alkaloid, a taxane, an epothilone, an intercalating agent, a signal transduction inhibitor, an apoptosis inducer, a cytokine, a chemokine, and a vaccine.

10. The method of claim 8, wherein the anti-tumor agent is selected from the group consisting of: cisplatin, cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes, cytochalasin B, gramicidin D, ethidium bromide, emetine, mitomycin, etoposide, tenoposide, vincristine, vinblastine, vinorelbine, colchicin, anthracyclines daunorubicin, dihydroxy anthracin dione, mitoxantrone, mithramycin, actinomycin D, adriamycin, 1-dehydrotestosterone, glucocorticoid, procaine, tetracaine, lidocaine, propranolol, puromycin, ricin, and maytansinoids, Gefitinib, Erlotinib, Lapatinib, Sorafenib, Sunitinib, Imatinib, Dasatinib, Nilotinib, temsirolimus, everolimus, rapamycin, Trastuzumab, Cetuximab, Panitumumab, Bevacizumab, Rituximab, and Tositumomab.

11. The method of claim 8, wherein the tumor is a solid tumor.

12. The method of claim 8, further comprising one or more of the following steps: biopsing the tumor tissue, imaging the tumor tissue, and evaluating the effect of the administration on the tumor tissue.

13. The method of claim 8, wherein the conjugate is administered intravenously.

14. The method of claim 8, wherein the polysaccharide preparation has anti-Xa activity and anti-IIa activity each less than 20 IU/mg.

15. The method of claim 8, wherein the polysaccharide preparation has anti-IIa activity of 1 IU/mg or less.

16. The method of claim 8, wherein the polysaccharide preparation has anti-Xa activity of less than 10 IU/mg.

17. The method of claim 8, wherein the polysaccharide preparation has less than 30% glycol split uronic acid residues.

18. The method of claim 8, wherein the polysaccharide chains of the polysaccharide preparation each have greater than 40% $U_{2S}H_{NS,6S}$ disaccharide residues.

19. The method of claim 8, wherein the polysaccharide preparation has a degree of desulfation less than 40%.

20. The method of claim 8, wherein the polysaccharide chains of the polysaccharide preparation each have no more than 3 glycol split uronic acid residues ($U_G$).

21. The method of claim 8, wherein the polysaccharide chains of the polysaccharide preparation have a 2,5-anhydromannitol residue at the reducing end.

22. The method of claim 8, wherein the polysaccharide chains of the polysaccharide preparation have a uronic acid at the non-reducing end.

23. The method of claim 8, wherein the polysaccharide chains of the polysaccharide preparation have a glycol split uronic acid at the non-reducing end.

24. The method of claim 8, wherein n is 1-3.

25. The method of claim 1, wherein the tumor is a sarcoma or carcinoma.

26. The method of claim 1, wherein the tumor is a carcinoma of the head, neck, pharynx, thyroid, lung, breast, lymph, gastrointestinal system, stomach, liver, pancreas, small intestine, colon and rectum, anal canal, genitals, genitourinary tract, bladder, central nervous system (CNS), neural cells, glial cells or skin; or the tumor is an oral, esophageal, renal, urothelial, ovarian, uterine, cervical, endometrial, prostate or testicular carcinoma.

27. The method of claim 8, wherein the tumor is a sarcoma or carcinoma.

28. The method of claim 8, wherein the tumor is a carcinoma of the head, neck, pharynx, thyroid, lung, breast, lymph, gastrointestinal system, stomach, liver, pancreas, small intestine, colon and rectum, anal canal, genitals, genitourinary tract, bladder, central nervous system (CNS), neural cells, glial cells or skin; or the tumor is an oral, esophageal, renal, urothelial, ovarian, uterine, cervical, endometrial, prostate or testicular carcinoma.

29. The method of claim 3, wherein the agent is a taxane.

30. The method of claim 29, wherein the taxane is paclitaxel or docetaxel.

31. The method of claim 8, wherein the agent is a taxane.

32. The method of claim 31, wherein the taxane is paclitaxel or docetaxel.

* * * * *